United States Patent [19]
Ornitz et al.

[11] Patent Number: 6,136,040
[45] Date of Patent: Oct. 24, 2000

[54] ANIMAL MODEL WITH DISRUPTED FGF-9 GENE

[75] Inventors: David M. Ornitz; Jennifer S. Colvin, both of St. Louis, Mo.

[73] Assignee: Washington University, St. Louis, Mo.

[21] Appl. No.: 09/256,546

[22] Filed: Feb. 24, 1999

Related U.S. Application Data

[60] Provisional application No. 60/076,954, Mar. 5, 1998.

[51] Int. Cl.[7] .......................... A01K 67/027; C12N 15/00
[52] U.S. Cl. ......................................... 8/18; 8/21
[58] Field of Search ....................... 800/8, 21, 3

[56] References Cited

U.S. PATENT DOCUMENTS 5,891,655   4/1999   Ornitz ..................................... 435/7.21

FOREIGN PATENT DOCUMENTS 9641523   12/1996   WIPO .

OTHER PUBLICATIONS

Seamark RF. Reprod. Fertil. Dev. 6:653–657, 1994.
Meredith RW et al. J. Mol. Med. 75:208–216, 1997.
Mullins LJ and Mullins JJ. J. Clin. Invest.97:1557–1560, 1996.

Ornitz, et al.; J. Biol. Chem., vol. 271, No. 25, pp. 15292–15297 (1996).

Naski, et al.; Nature Genetics, vol. 13 pp. 233–237 (1996).

Santos–Ocampo et al.; J. Biol. Chem. vol. 271, No. 3 pp. 1726–1731 (1996).

Colvin, et al.; Nature Genetics, vol. 12, pp. 390–397 (1996).

*Primary Examiner*—Jasemine Chambers
*Assistant Examiner*—Ram Shukla
*Attorney, Agent, or Firm*—Scott J. Meyer

[57] ABSTRACT

A unique animal model is disclosed which is useful for studying the role of FGF-9 activity in cardiovascular diseases. To provide this animal model, the FGF-9 gene is disrupted in mice, that is, null mutation in the mouse FGF-9 gene is engineered. This knockout mouse was produced by deleting the sequences immediately downstream of the initiation methionine in exon 1. Analysis of the FGF-9 null embryos demonstrates perinatal lethality with apparent pathology in lung and cardiac tissue.

3 Claims, 3 Drawing Sheets

H&E sections of littermate control (A) and FGF-9 null (B) mouse embryos at 14.5 days of gestation. L, lung; A, atria; V, ventricle.

ANIMAL MODEL WITH DISRUPTED FGF-9 GENE

This is a Continuation of application Ser. No. 60/076,954, filed Mar. 5, 1998.

BACKGROUND OF THE INVENTION

This invention relates to a member of the fibroblast growth factor family designated FGF-9 and, more particularly, to an animal model for studying the role of FGF-9 in the regulation of cardiovascular and pulmonary physiology and growth.

(Note: Literature references on the following background information and on conventional test methods and laboratory procedures well-known to the person skilled in the art, and other such state-of-the-art techniques as used herein, are indicated by reference numbers in brackets, and appended at the end of the specification).

The first fibroblast growth factor (FGF) discovered in the 1970s, now known as FGF-2, had an activity that stimulated the proliferation of 3T3 fibroblasts. The FGF family has subsequently grown to include fifteen structurally related proteins, namely FGFs 1–10, FHFs 1–4 (fibroblast growth factor homologous factors) [1,2] and FGF-15. FGFs 1–10 interact with four distinct high-affinity FGF receptors (FGFRs) with varying affinity and specificity [3].

Alternative mRNA splicing significantly modifies the binding specificities of FGF receptors 1–3 [4]. An additional mechanism regulating FGF activity involves heparin or heparan sulfate proteoglycans (HSPG), molecules which are required for ligand-receptor interactions in vitro and possibly in vivo.

By sequence analysis, FHFs 1–4 show significant amino acid homology with other members of the FGF family [1]. However, thus far FHFs do not have any biological activity towards the four known FGF receptors.

Both FGF ligands and receptors are expressed in specific spatial and temporal patterns during embryonic development. Different FGFs and FGFRs display both overlapping and unique patterns of expression raising the question of specific function and redundancy of function. These issues can be addressed by examining the phenotypic consequences of mutations in FGF ligands and receptors in both human and experimental animal models. As shown by Santos-Ocampo et al., J. Biol. Chem. 271, 1726–1731 (1996), receptor specificity is an essential mechanism of FGFs.

Several human genetic diseases result from dominant gain of function mutations in the genes encoding FGFR 1, 2 and 3. These disorders result in skeletal dysplasias and/or craniosynostosis and some of these diseases have associated distinct CNS abnormalities.

The genetic disorders involving FGF receptor 3 (FGFR3) (achondroplasia, thanatophoric dysplasia, hypochondroplasia) demonstrate that FGFR3 controls the rate of normal growth of the skeleton [5] and may be an important signaling molecule in the developing temporal lobe and hippocampus [6].

The genetic disease, Apert's syndrome, which results from a point mutation in the FGF receptor 2 gene, is also associated with skeletal, cardiovascular, genitourinary and CNS phenotypes [7].

The biologic response to an FGF ligand depends on the cell-type, tissue and developmental stage. FGF is required for survival and growth of endothelial cells [8], 3T3 cells [9], receptor-expressing lymphoid cells [10], neurons and muscle.

FGF-2 is also effective in maintaining certain hematopoietic lineages in long term primary bone marrow culture [11] and for the survival and possible differentiation of hematopoietic progenitor cells [12].

During embryonic development FGFs are thought to be important for the induction and patterning of mesoderm [13–15]. The diverse types of responses to FGF (cell growth, survival and differentiation) may result from the activity of alternative signaling pathways in different cell-types, or from committed cells responding differentially to a common signaling pathway.

In the cardiovascular system, both FGF-1 and FGF-2 are proven mitogens for vascular endothelial cells and vascular smooth muscle cells.

For example, following balloon catheter endarterectomy, endothelial cell outgrowth into the denuded area is significantly enhanced by intravenously administered FGF-2 [16]. Following vascular surgery of trauma, reendothelialization is often incomplete. This may contribute to prolonged vascular disease and the failure of some surgical procedures (reviewed in [17]). The ability of FGF-2 to enhance endothelial outgrowth may therefore be a useful therapeutic tool [17].

Similarly, after prolonged infusion, FGF-2 significantly enhances intimal thickening [17].

FGF-1 also causes intimal thickening when overexpressed in arteries in vivo [18].

Endotheial and vascular smooth muscle cell growth is complex and probably involves a balance between both positive and negative regulatory molecules. Although FGF-2 is present in the arterial wall and is produced by both endothelial cells and vascular smooth muscle, it has little effect on the growth of normal vascular endothelial cells [19].

Nevertheless, FGF can stimulate the growth of injured endothelium. Both FGF-1 and FGF-2 lack signal peptides and are released from cells by poorly defined mechanisms. One hypothesis that accounts for these features of FGF-1 and FGF-2 proposes that cell injury, cell migration and cell death may result in the release into the extracellular environment of FGF, which would mediate a physiological response [17,20].

Unlike FGFs 1 and 2, many of the other FGFs are efficiently secreted. The specific spatial and temporal patterns of expression of these FGFs along with a growing body of genetic evidence (mutant mice and knockout mice) suggest that these FGFs are essential regulators of embryonic development.

The precise role of FGF signalling in cardiovascular development is not known. However, the expression of both FGF ligands and receptors in both cardiac and vascular mesoderm and endoderm suggest an important role for these molecules in development.

Additionally, FGFs 1, 2 and 4 can support the proliferation and differentiation of chick precardiac myoblasts. This activity can be blocked by chlorate, a known inhibitor of FGF ligand-receptor interactions [21,22]. The knockout of FGF-2 in mice, surprisingly, has little or no developmental consequences. Mice lacking either FGF 4 or 8 die too early in embryonic development to allow analysis of the role of these factors in cardiovascular development. The knockout of FGF-3 causes early inner ear and axial skeletal phenotypes, and the knockout of FGF 5 or 7 results in abnormal hair growth [23–25].

The four FGF receptor genes have also been disrupted in mice. A null mutation in the FGFR1 gene results in early embryonic lethality. These mice die around the time of gastrulation. Analysis of these animals demonstrates possible patterning defects in axial mesoderm as well as general growth retardation [14,15].

These studies suggest that FGFR1 is essential for normal rates of mesodermal cell proliferation and migration. FGFR1 is expressed in a wide variety of tissues later in development, however the embryonic lethality of FGFR1 null mice precludes a determination of the role of FGFR1 at these times.

FGFR3 null mice demonstrate defects in skeletal growth and in inner ear development [26]. The skeletal phenotype suggests that FGFR3 is a negative regulator of endochondral ossification and the inner ear phenotype demonstrates that FGFR3 is essential for the normal development of supporting cells within the organ of Corti. FGFR3 is expressed in many other tissues. However, a phenotype in these tissues is not readily apparent. Therefore, the function of FGFR3 in these tissues may be subtle or redundant with other FGFRs.

FGFR2 and FGFR4 have also been disrupted in mice. FGFR2 null mice die early in embryogenesis and FGFR4 null mice have little or no apparent phenotype.

BRIEF DESCRIPTION OF THE INVENTION

In accordance with the present invention an animal model is provided for studying the role of FGF-9 in the regulation of cardiovascular and pulmonary physiology and growth. To provide this animal model, a null mutation in the mouse FGF-9 gene was engineered. This knockout mouse was produced by deleting the sequences that encode the 3' end of exon 1 which contains the initiation methionine.

Surprisingly, so far the FGF-9 gene is the only FGF gene that, when disrupted, shows a cardiac or pulmonary phenotype. Accordingly, the knockout mouse described and claimed herein provides a unique animal model for studying the role of FGF-9 activity in human cardiovascular and pulmonary diseases.

Analysis or FGF-9 null embryos demonstrates perinatal lethality with apparent pathology localized to lung and cardiac tissue. Preliminary analysis of the progeny of heterozygous crosses yielded no viable homozygous offspring. However, examination of 14.5 day mouse embryos revealed a normal Mendelian ratio of wild type, homozygous and heterozygous embryos. Histological examination of 14.5 day mouse embryos demonstrates an under-developed lung, and a dilated atrium (see FIG. 1). At the present stage of analysis no other phenotypes are readily apparent.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in conjunction with the accompanying drawings.

BRIEF DESCRIPTION OF THE DRAWINGS

FIG. 1 in two parts, A and B, shows the histological analysis of FGF-9 null mouse embryos compared to littermate control; both at 14.5 days of gestation. L,lung; A,atria; V, ventricle.

Top line, the full length FGF receptor with three Ig-like domains. The major alternative splicing pathways will express either Ig-like domain IIIb or IIIc.

The stippled region beginning in Ig-like domain III is the sequence subject to alternative splicing.

Middle line, short form of the FGF receptor expressing Ig-like domains II and III.

Bottom line, secreted form of the FGF receptor expressing Ig-like domains II and IIIa.

SP, signal peptide;

A, acidic amino acid domain;

I, II, III, Ig-like domains;

TM, transmembrane domain;

KI, kinase insert domain;

P, site of putative receptor authophosphorylation; s-s, disulfide bond.

Figure 3:
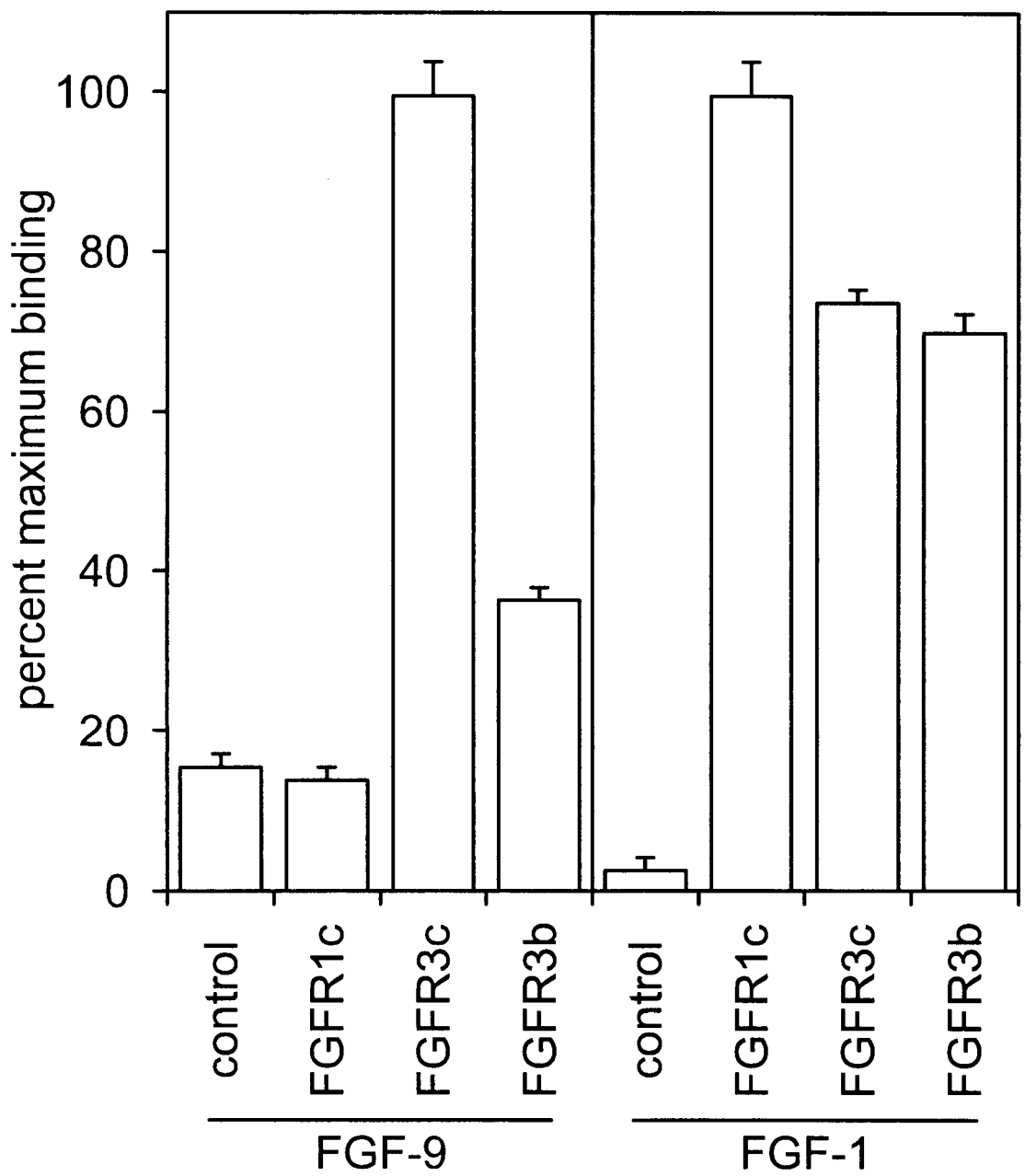

FIG. 3 is a bar chart which shows the binding of $^{125}$I-labeled FGF-9 or FGF-1 to soluble FGF receptors.

In order to further illustrate the invention, the following detailed examples are disclosed although it will be appreciated that the invention is not limited to these specific examples or the details therein.

EXAMPLES

Materials and Methods

FGF-9 and FGFR3 are co-expressed in brain and kidney. The detailed expression pattern of FGF-9 in other tissues is not known. In vitro, FGF-9 is a ligand for FGFR2 and FGFR3. These preliminary observations suggest that in vivo, FGF-9 is also a physiological ligand for these receptors.

To evaluate the developmental role of FGF-9, the FGF-9 gene was disrupted in mice. FGF-9 −/− mice are used to determine whether the activity of FGFR2 or FGFR3 is affected in tissues that co-express R2+R3 or R+R9 proteins. Mice containing a β-galactosidase gene inserted into the FGF-9 locus can be used to identify sites of FGF-9 expression.

The phenotypes in FGF-9 −/− mice are distinguished from those seen in FGFR3 −/− mice. These distinct phenotypes indicate that physiologically FGF-9 is signaling through another FGFR, believed to be FGFR2.

Several preliminary studies have been pursued prior to the knockout of FGF-9. These studies as set forth below define the FGF-9 gene structure (c) and chromosomal location (a) and suggest that no known mouse mutant for FGF-9 exists.

(a) Chromosomal mapping of FGF-9 in the mouse. Before proceeding with the knockout of FGF-9, the chromosomal location of FGF-9 was determined to rule out any known candidate mouse mutations. By comparing regions of synteny between mouse and human chromosomes one can also estimate the map position of human FGF-9. This helps to identify human genetic diseases that may involve the FGF-9 gene.

The FGF-9 locus was genetically mapped using recombinant inbred (RI) mouse strains [27]. Using the partial murine FGF-9 cDNA as a probe, Taq I restriction fragment length polymorphisms (RFLPs) have been identified between the C57BL/6J and DBA strains of mice.

DNA from 26 BXD RI strains, obtained from the Jackson Laboratory, Bar Harbor, Me., were cut with the restriction enzyme Taq I and probed with the FGF-9 cDNA.

The data obtained from this analysis localized FGF-9 to mouse chromosome 14 at the CTLA-6 locus. This region of chromosome 14 is interesting because it contains two other loci involving possible developmental phenotypes: DS (disorganized) and TG737 (resulting in polycystic kidney disease) [28,29].

To more precisely map the FGF-9 gene in this region, DNA from an interspecific backcross between M. musculus and C3H has been similarly analyzed. FGF-9 shows no recombinants with TF737 indicating that these genes are within 1 cm of each other. However, it is believed that FGF-9 and TG737 are unlikely to be allelic. No candidate human diseases currently map to the syntenic region on human chromosome 13.

(b) Expression patterns of FGF-9 during development and in the adult (specific result 1). RNase protection analysis of embryonic RNA demonstrates that FGF-9 is expressed in day 12.5 mouse embryos. It is also expressed in adult brain and kidney. Preliminary in situ hybridization experiments were done using partial cDNA probes. Rabbit polyclonal antibodies were made against biologically active recombinant FGF-9 (recombinant protein was sent to CALTAG, Inc. for injection into rabbits). These antibodies can be used to immunolocalize FGF-9 in both embryonic and adult tissues. Anti-peptide antibodies also were made and tested.

A second targeting construct (see below) was made in which the β-galactosidase gene was inserted into the first exon of the FGF-9 gene. This allows chimeric mice, or mice which have transmitted the mutant allele through the germline, to be analyzed for β-galactosidase expression patterns. This methodology has been used to study the patterns of several genes including the FGF-3/int-2 gene [23, 30].

(c) FGF-9 gene structure. A P1 containing the FGF-9 gene was obtained from a 129/SV library. DNA fragments have been subcloned, and three exons coding for the mature FGF-9 protein have been mapped. These clones have been used to construct gene-targeting vectors.

(d) Generation of mice lacking FGF-9 (specific result 2). To assess the role of FGF-9 in development and to determine whether it interacts with FGFR3 in a genetically defined pathway, a null allele for FGF-9 was introduced into the mouse germline using homologous recombination in embryonic stem cells.

FGF-9 is targeted by making a deletion including the 3' half of exon 1. Successful targeting of this exon, which contains the initiation methionine, resulted in a null allele for FGF-9. A targeting construct containing a pol-2 neo selection cassette [31], and two herpes virus thymidine kinase genes has been constructed. Two electroporations were carried out.

The first electroporation yielded no homologous recombinants out of 240 colonies screened.

The second electroporation has yielded four targeted cell lines out of 200 colonies screened.

These cells were introduced into mouse blastocysts to generate chimeras, which were bred to determine germline transmission.

As discussed above, in vitro studies show that FGF-9 can activate both FGFR2c and FGFR3c. Because these receptors appear to be co-expressed in developing glia, FGF-9 null mice and FGF-9/FGFR3 double null mice may allow a role of FGF signaling in glial development to be uncovered. Similarly, FGF-9/FGFR3 double mutants may uncover a kidney phenotype even when no phenotype is seen in the single knockout animals.

The methodologies for these procedures, though difficult, are well established [32, 33]. In our laboratory we have successfully targeted the FGFR3 gene. The initial analysis of FGF-9 recombinant embryonic stem cell clones uses DNA blot hybridizations.

After germline transmission of the FGF-9 targeted allele is achieved, heterozygous mice are bred to homozygosity and the offspring examined for a phenotype.

Targeting a β-galactosidase gene to the FGF-9 locus. To determine in situ where and when FGF-9 is expressed, a β-galactosidase gene was inserted into the FGF-9 genomic locus.

Like the original FGF-9 targeting construct, the β-galactosidase/FGF-9' construct generates a 0.5 kb deletion beginning 50 bp downstream of the ATG in exon 1 and extending into intron sequence; the construct contains 5 kb of 5' homologous sequence, 3.2 kb of 3' homologous sequence and 2 thymidine kinase genes for negative selection.

In the new construct, a β-galactosidase expression cassette is inserted in frame with FGF-9 sequence starting 50 bp from the ATG in exon 1.

A pol-2 neo selection cassette flanked by lox P sites [34] is inserted 3' of β-galactosidase. SM-1 embryonic stem cells were transfected with this targeting vector, selected in the presence of Geneticin (antibiotic G418) and FIAU [1-(2'-deoxy-2'-fluoro-β-D-arabinofuranosyl)-5-iodouracil], and screened for homologous recombination as described above. The lox-P sites allow the optional removal of the pol-2 cassette via expression of crerecombinase either in embryonic stem cells or by pronuclear injection into heterozygous oocytes [35, 37] or by mating. This allows analysis of β-galactosidase expression driven by the endogenous FGF-9 promoter without adjacent pol-2 promoter elements which may alter β-galactosidase expression.

(e) Determine sequence motifs in FGF receptor 3 that allow FGF-9 binding (specific result 3). Iodinated FGF-9 binds soluble FGFR3 ectodomain but not soluble FGFR1 ectodomain (FIG. 3). To map the region (s) in the FGFR binding domain that is required for ligand binding specificity, chimeric soluble receptors are constructed and assayed for FGF-9 binding activity. Pilot experiments indicate that sequence elements within Ig-like domain 2 may confer FGF-9 binding specificity to FGFR3.

This is in contrast to FGF-2 and 7 in which specificity is determined by sequences within Ig-like domain III. The knowledge gained from these experiments facilitates the development of reagents that specifically can mimic or antagonize an FGF ligand.

This type of structure-function information is useful in designing drugs that modulate FGF-FGF receptor binding and in understanding their mechanism of action. The specificity of such drugs allows diseases that involve FGFs to be treated with minimal side effects.

The experimental approaches to investigate the primary sequence requirements for ligand binding specificity involve deletion mutagenesis, construction of chimeric receptors and point mutagenesis. The following set of experiments use soluble receptors in which the extracellular region is fused in frame to alkaline phosphatase.

The soluble FGF receptor-AP binding assay [3, 39] is used for screening purposes, because of the ease in expression the soluble receptor in COS-7 cells and in performing the binding assay. Informative mutant proteins identified in the primary screen are reconstructed into full-length receptors and are assayed for biologic activity in growth factor-dependent lymphoid cells.

Figure 1A:
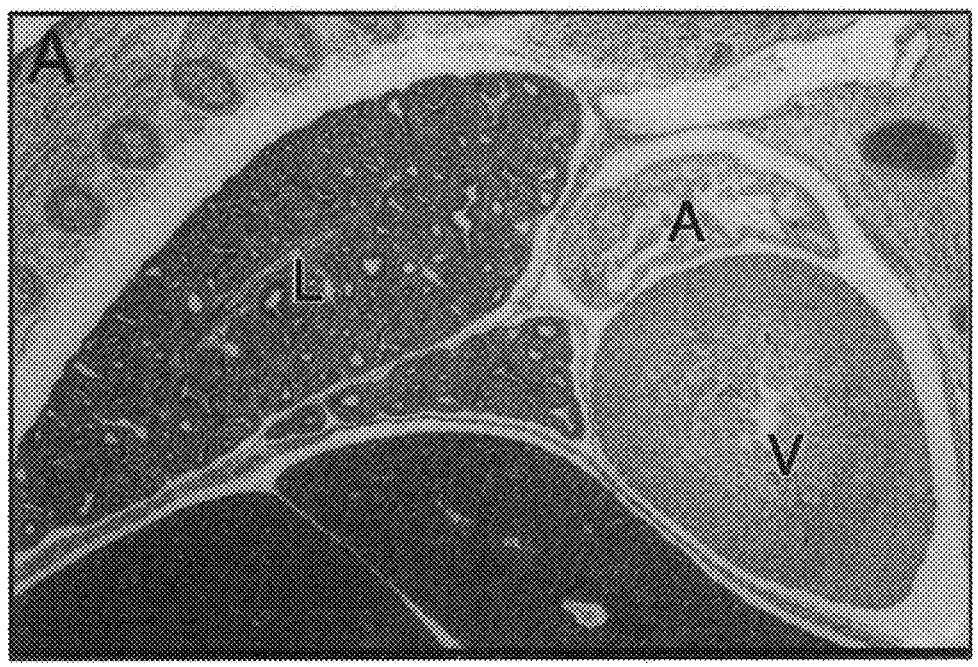
FIG. 1A, H&E sections of littermate control.
Figure 1B:
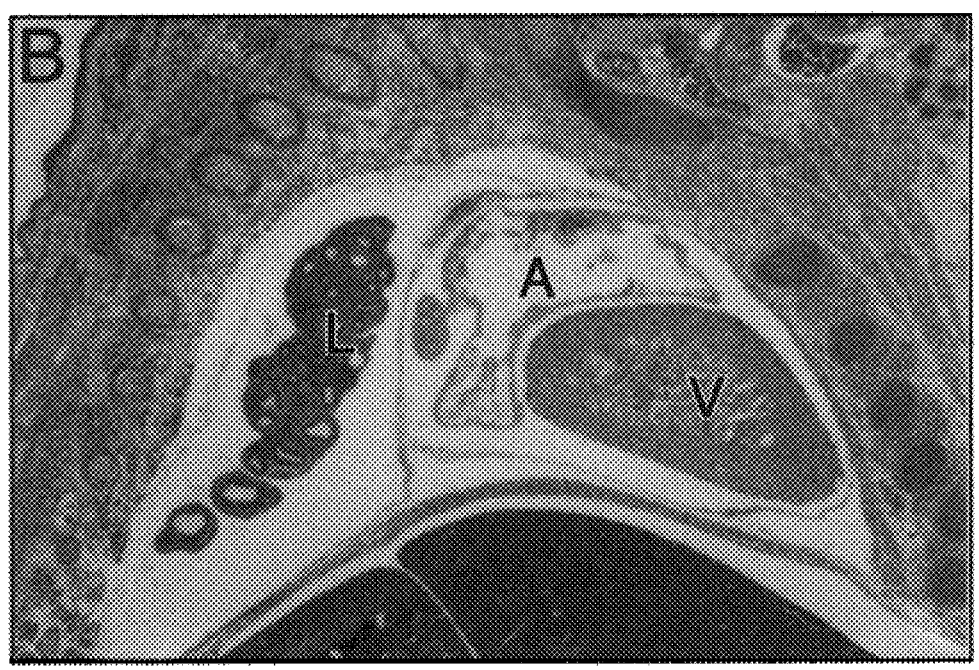
FIG. 1B, H&E sections of FGF-9 null mouse embryos.
Figure 2:
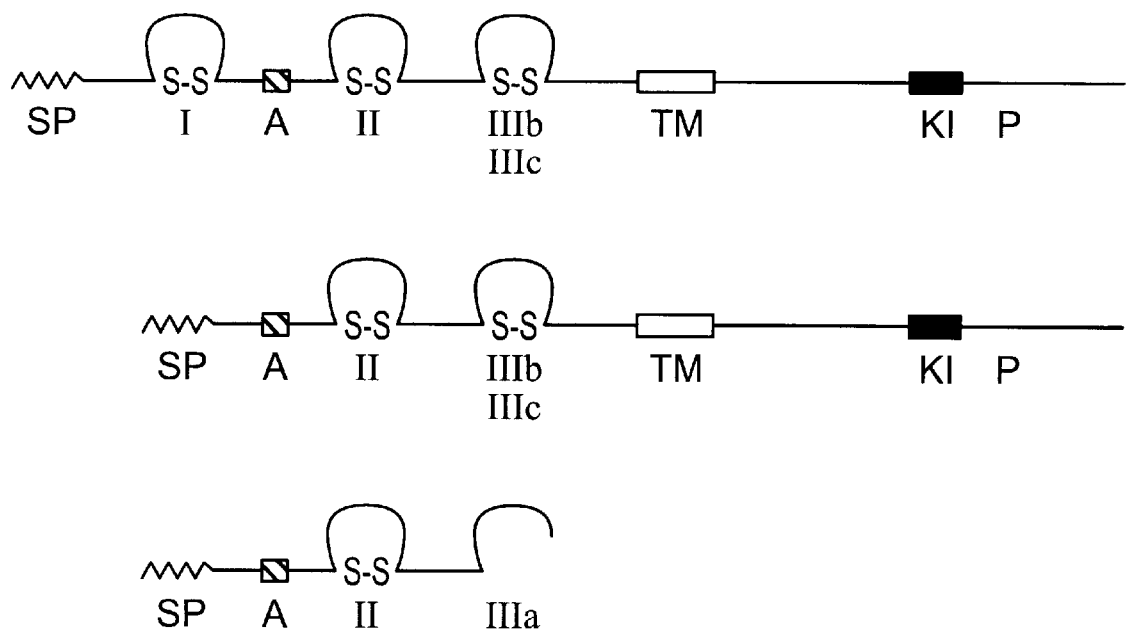
FIG. 2 shows the primary structure of FGF receptors.

Deletion mutagensis. Amino terminal deletions of FGF receptor 1 and 3 remove Ig-like domain I, the region between Ig-like domain I and II and Ig-like domain II (FIG. 1). This series of constructs tests the functional importance of Ig-like domain I and the acidic amino acid domain and define a minimal functional binding domain. Binding to these constructs is assayed with $^{125}$I-FGF-9.

Chimeric receptor mutagensis. A series of constructs create chimeric proteins between extracellular regions of FGFRs 1 and 3. Specific constructs replace sequences from FGFR 1 with homologous sequences from FGFR 3. These constructs show an increased affinity for FGF-9 as FGFR 1 sequence is replaced by FGFR 3 sequence. Assembly is by PCR, PCR mutagenesis and PCR ligation, and is confirmed by DNA sequencing.

Chimeric scanning mutants. To compliment the above experiments and to define critical sequence elements required for ligand binding specificity, a series of chimeric scanning mutants are constructed. These chimeric proteins replace smaller regions of FGFR 1 with homologous sequence derived from FGFR 3. When a short peptide sequence is responsible for ligand binding specificity, then a subset of this series of chimeric receptors shows an increased affinity for FGF-9. Such regions are further analyzed by alanine scanning mutagenesis (introduction of alanine point mutations), a method that has been used successfully to define the binding properties of human growth hormone [38].

(f) The significance of FGF-9 and mice lacking the FGF-9 gene. The pathophysiological significance of FGF-9 is poorly defined. However, its expression has been detected in 37 percent of primary human mammary tumors (out of a sample of 103 consecutive tumor resections) [40].

FGF-9 was discovered as a growth factor activity in human glioma-derived cell lines (FGF-9 was originally named glial activating factor (GAF) [41]. Thus FGF-9 may have a role in the development of progression of human cancers.

GAF/FGF-9 was found to be mitogenic for oligodendrocytes, 3T3 cells and PC-12 cells, but not for endothelial cells [41].

The lack of activity towards endothelial cells is interesting and consistent with recently published data [42], showing that recombinant FGF-9 is a poor ligand for FGFR1, which is the only known FGF receptor expressed on endothelial cells.

In the adult, FGF-9 is expressed in the central nervous system (CNS) and the kidney. A recent in situ hybridization study demonstrates that FGF-9 is expressed in the adult CNS in specific neuronal nuclei in a pattern that differs from that of others FGFs [43]. Its expression pattern in the embryo is unknown. However, preliminary data indicates that it is expressed in precartilaginous condensations where it may activate FGFR3.

The data (Table 1) [42] demonstrates that FGF-9 efficiently activates the "b" and "c" splice forms of FGFR3 and the "c" splice form of FGFR2. FGF-9 thus becomes the first selective ligand for FGFR3b (FGF-1 activates all FGF receptors).

It is of interest to determine whether this specific ligand-receptor pair is physiologically relevant. The role of FGF-9 in chondrogenesis can be examined in the mice lacking the FGF-9 gene as described herein, and examining chondrogenesis in day 16 to 18 mouse embryos.

Because FGF-9, FGFR2 and FGFR3 are prominently expressed in the CNS of adult mice, and FGF-9 and FGFR 3 are also prominently expressed in the kidney, it is possible that FGF-9, FGFR 2 and FGFR 3 form physiologically or developmentally relevant ligand-receptor pairs in these tissues.

A phenotype in mice lacking the FGF-9 gene can identify sites where signaling between FGF-9 and FGFR2 and/or FGFR3 is important.

Although no human diseases have thus far been associated with FGF-9, the extremely high degree of conservation between the mouse and human genes does suggest an essential developmental or physiological role in humans.

The genetic mapping of the FGF-9 gene can facilitate linking this gene to potential human diseases.

TABLE I

| FGFR | Ligand* | | | | | | | | |
|---|---|---|---|---|---|---|---|---|---|
| | FGF-1 | FGF-2 | FGF-3 | FGF-4 | FGF-5 | FGF-6 | FGF-7 | FGF-8 | FGF-9 |
| 1b | 100 | 59.9 | 34.3 | 15.6 | 3.8 | 4.6 | 6.3 | 3.5 | 3.5 |
| 1c | 100 | 103.9 | 0.3 | 102.3 | 59.0 | 54.9 | 0.3 | 0.7 | 21.1 |
| 2b | 100 | 9.0 | 44.6 | 14.9 | 5.0 | 5.4 | 80.6 | 3.8 | 7.3 |
| 2c | 100 | 63.9 | 4.2 | 94.3 | 25.0 | 60.7 | 2.5 | 16.1 | 89.2 |
| 3b | 100 | 1.2 | 1.5 | 1.0 | 1.0 | 0.9 | 1.2 | 0.9 | 41.5 |
| 3c | 100 | 107.2 | 0.6 | 69.1 | 11.8 | 8.8 | 1.0 | 40.5 | 95.6 |
| 4Δ | 100 | 94.6 | 7.2 | 64.7 | 6.3 | 42.0 | 1.7 | 69.4 | 60.3 |

*FGF receptor activation by FGFs 1–9. Relative mitogenic activity of BaF$_3$cell lines expressing the indicated FGFR (26, 38, 99). Mitogenic activity (calculated as the average of the ratio of $^3$H-thymidine incorporated at 312 and 1250 pM FGF to 0 pM FGF) was normalized to that for FGF-1 for each receptor-expressing cell line. FGFRs 1–3 are three Ig-like domain forms, FGFR4Δ is the 2 Ig-like domain form.

Various other examples will be apparent to the person skilled in the art after reading the present disclosure without departing from the spirit and scope of the invention. It is intended that all such other examples be included within the scope of the appended claims.

What is claimed is:

1. A transgenic knockout mouse whose genome comprises an introduced null mutation in the FGF-9 gene, wherein said mouse exhibits under-developed lungs and dilated atrium in 14.5 day old embryos.

2. A transgenic knockout mouse, wherein both alleles of the FGF-9 gene of said mouse have been disrupted by deleting the entire exon 1 sequence including the initiation codon, and wherein said mouse exhibits under-developed lungs and a dilated atrium.

3. A method of making a homozygous transgenic knockout mouse whose genome comprises a disrupted FGF-9 gene, comprising the steps of:

deleting the first exon of the FGF-9 gene including the initiation codon by homologous recombination in mouse embryonic stem cells;

introducing said embryonic stem cells into a mouse blastocyst and transplanting said blastocyst into a pseudopregnant mouse;

allowing said blastocyst to develop into a chimeric mouse;

breeding said chimeric mouse to produce offspring; and screening said offspring to identify a homozygous transgenic knockout mouse whose genome comprises deletion of the first exon of both alleles of the FGF-9 gene, and wherein said mouse exhibits under-developed lungs and a dilated atrium.

* * * * *

UNITED STATES PATENT AND TRADEMARK OFFICE
CERTIFICATE OF CORRECTION

PATENT NO. : 6,136,040
DATED : October 24, 2000
INVENTOR(S) : David M. Ornitz and Jennifer S. Colvin It is certified that error appears in the above-identified patent and that said Letters Patent is hereby corrected as shown below:

Column 2,
Line 25, "Endotheial" should read -- Endothelial --.

Signed and Sealed this

First Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,136,040
DATED         : October 24, 2000
INVENTOR(S)   : David M. Ornitz et al.

It is certified that error appears in the above-identified patent and that said Letters Patent is hereby corrected as shown below:

Title page,
Item [56], insert the following References Cited:

1. Coulier, F., Pontarotti, P., Roubin, R., Hartung, H., Goldfarb, M., and Birnbaum, D. (1997). *J. Mol. Evol.* 44 (1), 43-56.

2. Yamasaki, M., Miyake, A., Tagashira, S., and Itoh, N. (1996). *J. Biol. Chem.* 271 (27), 15918-15921.

3. Ornitz, D.M., and Leder, P. (1992) *J. Biol. Chem.* 267, 16305-16311.

4. Ornitz, D.M., Xu, J., Colvin, J.S., McEwen, D.G., MacArthur, C.A., Coulier, F., Gao, G., and Goldfarb, M. (1996) *J. Biol. Chem.* 271 (25) 15292-15297.

5.. Naski, M.C., Wang, Q., Xu, J., and Ornitz, D.M. (1996) *Nature Genet.*, 13, 233-237.

6. Coulter, C.L., Leech, R.W., Brumback, R.A., and Schaefer, G.B. (1991) *Childs Nervous System* 7(1), 21-6.

7. Cohen, M.M., Jr., and Kreiborg, S. (1993) *Am. J. Dis. Child.* 147(9), 989-93.

8. Jaye, M., Howk, R., Burgess, W., Ricca, G.A., Chiu, I.-M., Ravera, M.W., O'Brien, S.J., Modi, W.S., Maciag, T., and Drohan, W.N. (1986) *Science* 233, 541-545.

9. Tamm, I., Kikuchi, T., and Zychlinsky, A. (1991) *Proc. Natl. Acad. Sci. USA* 88, 3372-3376.

10. Bernard, O., Li, M., and Reid, H.H. (1991) *Proc. Natl. Acad. Sci USA* 88, 7625-7629.

11. Wilson, L.E., Rifkin, D.B., Kelly, F., Hannocks, M.-J. and Gabrilove, J.L. (1991) *Blood* 77(5), 954-960.

12. Katoh, O., Hattori, Y., Sato, T., Kimura, A., Kuramoto, A., Sugimura, T., and Terada, M. (1992) *Biochem. Biophys. Res. Comm.* 183(1), 83-92.

13. Slack, J.M.W., Darlington, B.G., Heath, J.K., and Godsave, S.F. (1987) *Nature* 326, 197-200.

14. Deng, C.X., Wynshaw-Boris, A., Shen, M.M., Daugherty, C., Ornitz, D.M., and Leder, P. (1994). *Genes Dev.* 8, 3045-3057.

15. Yamaguchi, T.P., Harpal, K., Henkemeyer, M., and Rossant, J. (1994) *Genes Dev.* 8, 3032-3044.

UNITED STATES PATENT AND TRADEMARK OFFICE
CERTIFICATE OF CORRECTION

PATENT NO. : 6,136,040
DATED : October 24, 2000
INVENTOR(S) : David M. Ornitz et al.

It is certified that error appears in the above-identified patent and that said Letters Patent is hereby corrected as shown below:

16. Lindner, V., Lappi, D.A., Baird, A., Majack, R.A., and Reidy, M.A., (1991) *Circ. Res.* 68(1), 106-13.

17. Lindner, V., and Reidy, M.A., (1991) *Proc. Natl. Acad. Sci USA* 88(9), 3739-43

18. Nabel, E., Yang, Z., Plautz, G., Forough, R., Zhan, X., Haudenschild, C., Maciag, T., and Nabel, G. (1993) *Nature* 362, 844-846.

19. Reidy, M.A., Fingerle, J., and Lindner, V. (1992) *Circulation* 86, suppl. III, 43-46.

20. Cheng, G.C., Briggs, W.H., Gerson, D.S., Libby, P., Grodzinsky, A.J., Gray, M.L., and Lee, R.T. (1997) *Circulation Research* 80(1), 28-36.

21. Rapraeger, A.C., Krufka, A., and Olwin, B.B. (1991) *Science* 252, 1705-1708.

22. Zhu, X.L., Sasse, J., McAllister, D., and Lough, J. (1996) *Devel. Dynamics* 207(4) 429-438.

23. Mansour, S., Goddard, J., and Capecchi, M. (1993) *Development* 117, 13-28.

24. Guo, L., Degenstein, L., and Fuchs, E. (1996) *Genes Dev.* 10, 165-175.

25. Hèbert, J.M., Rosenquist, T., Götz, J., and Martin, G.R. (1994) *Cell* 78, 1017-1025.

26. Colvin, J.S., Bohne, B.A., Harding, G.W., McEwen, D.G. and Ornitz, D.M. (1996) *Nature Genet.* 12, 390-397

27. B.A. Taylor, *Academic Press*, New York; H.C. Morse, III, ed., 423-438 (1978).

28. J.H. Moyer, et al., *Science* 264, 1329-1333 (1994).

29. J.L. Crosby, R.C. Bleackley, J.H. Nadeau, *Genomics* 6, 252-259 (1990).

30. S.L. Mansour, K.R. Thomas, C.X. Deng, M.R. Capecchi, *Proc Natl Acad Sci U S A* 87, 7688-92 (1990).

31. A.P. Davis, M.R. Capecchi, *Development* 120, 2187-2198 (1994).

32. E.J. Robertson, *Teratocarcinomas and embryonic stem cells: A practical approach.* D. Rickwood, B.D. Hames, Eds., Practical Approach Series (IRL Press, Washington, D.C. 1987).

33. A. Nagy, J. Rossant, R. Nagy, W. Abramow-Newerly, J.C. Roder, *Proc. Natl. Acad. Sci USA*, 90, 8424-8428 (1993).

UNITED STATES PATENT AND TRADEMARK OFFICE
CERTIFICATE OF CORRECTION

PATENT NO.   : 6,136,040
DATED        : October 24, 2000
INVENTOR(S)  : David M. Ornitz et al.

It is certified that error appears in the above-identified patent and that said Letters Patent is hereby corrected as shown below:

34. H. Gu, Y.R. Zou, K. Rajewsky, *Cell*, 73, 1155-64 (1993).

35. D. Metzger, J. Clifford, H. Chiba, P. Chambon, *Proc. Natl. Acad. Sci USA* 92, *6991-6995 (1995)*.

36. K. Araki, M. Araki, J. Miyazaki, P. Vassalli, *Proc. Natl. Acad. Sci USA* 92, 160-164 (1995).

37. F. Schwenk, U. Baron, K. Rajewsky, *Nucleic Acids Res.* 23, 5080-1 (1995).

38. B.C. Cunningham, J.A. Wells, *Science* 244, 1081-1085 (1989).

39. D.M. Ornitz, et al., *Mol. Cell. Biol.* 12, 240-247 (1992).

40. Penault-Llorca, F., Bertucci, F., Adelaid, J., Parc, P., Coulier, F., Jacquemier, J., Birnbaum, D. and deLapeyriere, O. (1995). Expression of FGF and FGF receptor genes in human breast cancer. *Int. J. Cancer* 61, 170-176.

41. Nauo, K., Seko, C., Kuroshima, K., Matsutani, E., Sasada, R., Kondo, T. and Kurokawa, T. (1993). Novel secretory heparin-binding factors from human glioma cells (Glia-activating factors) involved in glial cell growth. *J. Biol. Chem.*, 268, 2857-2864.

42. Santos-Ocampo, S., Colvin, J.S., Chellaiah, A.T., and Ornitz., D.M. (1996). Expression and biological activity of mouse fibroblast growth factor-9 (FGF-9). *J. Biol. Chem.*, 271, 1726-1731.

43. Tagashira, S., Ozaki, K., Ohta, M. and Itoh, N. (1995). Localization of fibroblast growth factor-9 mRNA in the rat brain. *Molec. Brain Res.* 30, 233-241.

Signed and Sealed this

Eighteenth Day of March, 2003

JAMES E. ROGAN
*Director of the United States Patent and Trademark Office*